US008129168B2

(12) United States Patent
Muller-Greven et al.

(10) Patent No.: US 8,129,168 B2
(45) Date of Patent: Mar. 6, 2012

(54) RECOMBINANT COLWELLIA PSYCHRERYTHRAEA ALKALINE PHOSPHATASE AND USES THEREOF

(75) Inventors: Jeannine C. Muller-Greven, Mentor, OH (US); Marc A. Post, Beachwood, OH (US); Christopher J. Kubu, Twinsburg, OH (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 12/687,677

(22) Filed: Jan. 14, 2010

(65) Prior Publication Data

US 2010/0184156 A1   Jul. 22, 2010

Related U.S. Application Data

(60) Provisional application No. 61/144,529, filed on Jan. 14, 2009.

(51) Int. Cl.
 C12N 1/20 (2006.01)
 C12N 15/00 (2006.01)
 C12P 1/00 (2006.01)
 C07H 21/00 (2006.01)
(52) U.S. Cl. .................. 435/252.3; 435/320.1; 435/41; 435/91.2; 536/23.1
(58) Field of Classification Search ........................ None
 See application file for complete search history.

(56) References Cited

U.S. PATENT DOCUMENTS

| 5,707,853 | A  | 1/1998 | Millan |
| 5,741,676 | A  | 4/1998 | Fuller |
| 5,756,285 | A  | 5/1998 | Fuller |
| 5,773,226 | A  | 6/1998 | Millan |
| 6,379,940 | B2 | 4/2002 | Moffett et al. |
| 6,387,634 | B2 | 5/2002 | Moffett et al. |
| 7,319,014 | B2 | 1/2008 | Guthrie et al. |
| 7,323,325 | B2 | 1/2008 | Nilsen et al. |

FOREIGN PATENT DOCUMENTS

JP    2002360259    12/2002

OTHER PUBLICATIONS

Asgeirsson et al., "Alkaline phosphatase from Atlantic cod (*Gadus morhua*). Kinetic and structural properties which indicate adaptation to low temperatures," Comparative Biochemistry and Physiology Part B: Biochemistry and Molecular Biology, 110(2): 315-329 (1995).
de Prada and Brenchley, "Purification and characterization of two extracellular alkaline phosphatases from a psychrophilic *Arthrobacter* isolate," Applied and Environmental Microbiology, 63(7): 2928-2931 (1997).
Feller and Gerday, "Psychrophilic enzymes: molecular basis of cold adaptation," Cellular and Molecular Life Sciences, 53: 830-841 (1997).
Hauksson et al., "Heat-labile bacterial alkaline phosphatase from a marine *Vibrio* sp." Enzyme and Microbial Technology, 27: 66-73 (2000).
Ishida et al., "Characteristics of psychrophilic alkaline phosphatase," Bioscience, Biotechnology, and Biochemistry, 62: 2246-2250 (1998).
Lee and Chuang, "Characterization of different molecular forms of alkaline phosphatase in the hepatopancreas from the shrimp *Penaeus monodon* (Crustacea: Decapoda)," Comparative Biochemistry and Physiology Part B: Comparative Biochemistry, 99(4): 845-850 (1991).
Olsen et al., "Alkaline phosphatase from the hepatopancreas of shrimp (*Pandalus borealis*): A dimeric enzyme with catalytically active subunits," Comparative Biochemistry and Physiology Part B: Comparative Biochemistry, 99(4): 755-761 (1991).
Olsen et al., "Recovery of Enzymes from Shrimp Waste," Process Biochemistry, 25: 67-68 (1990).
Rina et al., "Alkaline phosphatase from the Antarctic strain TAB5," Eur. J. Biochem., 267: 1230-1238 (2000).
Sambrook et al., "Molecular Cloning, A Laboratory Manual," Cold Spring Harbor Laboratory Press, pp. 1.53-1.73 (1989).
Shandilya and Chatterjee, "An engineered thermosensitive alkaline phosphatase for dephosphorylating DNA," Focus, 17(3): 93-95 (1995).
Whitmore and Goldberg, "Trout intestinal alkaline phosphatases. II. The effect of temperature upon enzymatic activity in vitro and in vivo," Journal of Experimental Zoology, 182(1): 59-68 (1972).
Chaidaroglou et al., "Function of Arginine-166 in the Active Site of *Escherichia coli* Alkaline Phosphatase," Biochemistry, 27: 8338-8343 (1988).
Christen et al., "Sequential Chemical Modifications of Tyrosyl Residues in Alkaline Phosphatase of *Escherichia coli*," Biochemistry, 10(8): 1377-1384 (1971).
Du et al., "Artificial Evolution of an Enzyme Active Site: Structural Studies of Three Highly Active Mutants of *Escherichia coli* Alkaline Phosphatase," Journal of Molecular Biology, 316(4): 941-953 (2002).
Dubose and Hartl, "The Molecular Evolution of Bacterial Alkaline Phosphatase: Correlating Variation among Enteric Bacteria to Experimental Manipulations of the Protein," Molecular Biology and Evolution, 7(6): 547-577 (1990).
Ghosh et al., "Modification of the Active Site of Alkaline Phosphatase by Site-Directed Mutagenesis," Science, 231: 145-148 (1986).

(Continued)

Primary Examiner — Tekchand Saidha
Assistant Examiner — MD. Younus Meah
(74) Attorney, Agent, or Firm — Steven M. Yee

(57) ABSTRACT

A heat labile alkaline phosphatase enzyme and methods of using the same and kits including the same are disclosed. Specifically, a nucleotide sequence of, peptide sequence of, methods of using, and kits comprising, a heat labile alkaline phosphatase isolated from *Colwellia psychrerythraea* are provided. Methods of over-expression and purification of the recombinant alkaline phosphatase and mutants thereof are also disclosed. Methods of over-expressing and purifying commercially useful quantities of active recombinant heat labile alkaline phosphatase fusion enzymes from *C. psychrerythraea*, wherein the fusion enzymes comprise one or more heterologous leader sequences are disclosed. The disclosed *C. psychrerythraea* heat labile alkaline phosphatase has properties similar to shrimp alkaline phosphatase and can be substituted for shrimp alkaline phosphatase in assays involving the same.

13 Claims, 4 Drawing Sheets

OTHER PUBLICATIONS

Ito et al., "Retention at the *cis*-Golgi and delayed degradation of tissue-non-specific alkaline phosphatase with an Asn$^{153}$ → Asp substitution, a cause of perinatal hypophosphatasia," Biochemical Journal, 361: 473-480 (2002).

Kozlenkov et al., "Residues Determining the Binding Specificity of Uncompetitive Inhibitors to Tissue-Nonspecific Alkaline Phosphatase," Journal of Bone and Mineral Research, 19(11): 1862-1872 (2004).

Lowe, "Site-specific Mutations in the COOH-Terminus of Placental Alkaline Phosphatase: A Single Amino Acid Change Converts a Phosphatidylinositol-glycan-anchored Protein to a Secreted Protein," The Journal of Cell Biology, 116(3): 799-807 (1992).

Millán, "Molecular Cloning and Sequence Analysis of Human Placental Alkaline Phosphatase," The Journal of Biological Chemistry, 261(7): 3112-3115 (1986).

Wang and Kantrowitz, "Trapping the tetrahedral intermediate in the alkaline phosphatase reaction by substitution of the active site serine with threonine," Protein Science, 15: 2395-2401 (2006).

Wang et al., "Metal Specificity Is Correlated with Two Crucial Active Site Residues in *Escherichia coli* Alkaline Phosphatase," Biochemistry, 44: 8378-8386 (2005).

FIGURE 2A

ATGAAAAAACTACTTTCCGCCGTTTTTGTCACCCTCACATTGGGTGCTTGTACTACCACTGAACAGTCTA
GTGATATTTCATCTGATAACTCAGTAGCCCCAAATTCACAAAGCAGCCCTAAAAATATCATCATGATCGT
AGGCGATGGTATGGGACCAGCTTATACCACTGCTTATCGTTATTTCAATGATGACCCGACAACAGCTGAA
ATTGAACAAAGTGTATTTGATAAACATTATGTCGGCTCAAGTAGTACCTACCCAGCAAAAATGTCTGGGT
ACATCACTGATTCAGCTGCTGCTGCAACAGCGCTAGCGACAGGTGTAAAAACTTATAATGATGCGATATC
TGTTGATACTAATAAAAAGTCGCTTTTGACTGTTTTAGAGTGGGCCAAACAGCAAGGTAAAAAAACAGGT
GTCGTTGTTACTTCTCAGATAAATCATGCAACTCCTGCCTCTTATCTTTCTCATAATGAAAACAGAAATA
ACTATAACGCTATTGCTGATAGTTATATCGACAATGGCATAAAAGCCGATGTTTATTTTGGTGGCGGCTG
GAAATACTTTATTCGAGAAGACCGTAATTTAGTCAACGAATTTAAAGCAGCTGGTTTTCAATATATAGAT
GATTATAAACAATTATCAACACTGAAATTAAATAAACCGGTACTCGGTCTTTTTGGCGATAGCGGTTTAC
CTTGGGCCCTAGACGATAAAGAAAAACATCGTTTGTCGTTAATGACAAAGGCAGCTACAAAACAGCTTAA
AAATCCCAATGGTTACTTTATGTTAGTTGAAGCCAGTCAAATCGATTGGGGTGGACATGGACGAGATATT
GGCGCGGCTATGGCTGAAATGGACGACCTTGCAAAAACAATCGCTTTTCTAGAAGAGTATGTCGCTAAAA
ATCCAGATACCTTAGTTGTACTTACAGCAGATCATAGTACAGGAGGCCTCAGTATTGGAAGAAAAACAGC
TATGTCTAACAAAGACATACACAGTAAATATTTATGGCAACCTGAGATACTACGAACACTGCCCCTTTCT
CCTGAAACGTTTGCCAAAACCTTTGCTAACAACAACCTGACTCTGCAACAGGTCAATGAGGTATTAAAGT
TTGAGATATCTTCTGATGATATGGCGTTGTTATTACAGTCAAAAAAAGAGGGTATAAAAATATACCAACA
GTTATCAGCAGAACAAAAACAAAAAAAATGGGCACCTAAAGCTGAAGGACCTATTTTGATAGCAATTAAA
AAAATCATAGACATAAAGACAAACACTGGCTGGGGTTCAATTAGTCATTCGGGTACACATACCGCAGTGG
ATGTACCCGTCTATGCCTTTGGTAAAGGAAGTGAGCAATTTAAGGGGCAAATAGATAATACTGATATTGC
CAAAAAGATATTTACTTTACTAGGTAAAAAGTAG

FIGURE 2B

```
  1  MKKLLSAVFV  TLTLGACTTT  EQSSDISSDN  SVAPNSQSSP  KNIIMIVGDG  MGPAYTTAYR
 61  YFNDDPTTAE  IEQSVFDKHY  VGSSSTYPAK  MSGYITDSAA  AATALATGVK  TYNDAISVDT
121  NKKSLLTVLE  WAKQQGKKTG  VVVTSQINHA  TPASYLSHNE  NRNNYNAIAD  SYIDNGIKAD
181  VYFGGGWKYF  IREDRNLVNE  FKAAGFQYID  DYKQLSTLKL  NKPVLGLFGD  SGLPWALDDK
241  EKHRLSLMTK  AATKQLKNPN  GYFMLVEASQ  IDWGGHGRDI  GAAMAEMDDL  AKTIAFLEEY
301  VAKNPDTLVV  LTADHSTGGL  SIGRKTAMSN  KDIHSKYLWQ  PEILRTLPLS  PETFAKTFAN
361  NNLTLQQVNE  VLKFEISSDD  MALLLQSKKE  GIKIYQQLSA  EQKQKKWAPK  AEGPILIAIK
421  KIIDIKTNTG  WGSISHSGTH  TAVDVPVYAF  GKGSEQFKGQ  IDNTDIAKKI  FTLLGKK
```

RECOMBINANT COLWELLIA PSYCHRERYTHRAEA ALKALINE PHOSPHATASE AND USES THEREOF

RELATED APPLICATIONS

This application claims priority to U.S. Provisional Patent Application No. 61/144,529, filed Jan. 14, 2009, the entire disclosure of which is incorporated herein by reference for all purposes.

FIELD OF THE INVENTION

Disclosed is a heat labile alkaline phosphatase enzyme and methods of using the same and kits including the same. Specifically, disclosed are nucleic acid sequences of, peptide sequences of, methods of using, and kits comprising, a heat labile alkaline phosphatase from *Colwellia psychrerythraea*.

BACKGROUND OF THE INVENTION

The phosphatase enzyme catalyzes the hydrolysis of phosphate groups, removing phosphates from various substrates. Within the family of phosphatase enzymes there exist members that are particularly active under alkaline pH conditions. Such phosphatases are commonly referred to as alkaline phosphatases. Still further, within this sub-family of alkaline phosphatases there are members that are particularly unstable at temperatures above 37° C. Such phosphatases are referred to generally as heat labile alkaline phosphatases.

Alkaline phosphatases (E.C. 3.1.3.1) are also commonly referred to as alkaline phosphomonoesterase, phosphomonoesterase or glycerophosphatase. These enzymes are orthophosphoric-monoester phosphohydrolases with enzyme activity optima at alkaline conditions. Examples of alkaline phosphatase substrates are deoxyribonucleic acid (DNA), ribonucleic acid (RNA), and ribo-, as well as deoxyribo-, nucleoside triphosphates, alkaloids and phosphate-containing proteins or polypeptides. The hydrolysis reaction catalyzed by phosphatase enzymes yields an alcohol and an orthophosphate. In other words, alkaline phosphatases dephosphorylate DNA, RNA, rNTPs and dNTPs. Dephosphorylation of protein by various alkaline phosphatases have also been reported. Alkaline phosphatases may be found in organisms ranging from bacteria to humans. Complex organisms may contain tissue-specific and non-tissue specific alkaline phosphatases. Alkaline phosphatases generally range in size from 15 kDa to 170 kDa. Some of these proteins are bound or "anchored" to cellular membranes. Alkaline phosphatases may require various co-factors for optimal activity, such as metal cations, like $Mg^{2+}$, $Zn^{2+}$ or $Co^{2+}$.

Alkaline phosphatases are often used in molecular biology applications, such as: 1) dephosphorylation of vector DNA after restriction enzyme digestions to minimize self-ligation of the cloning vector, thus favoring ligation of the insert to the vector and creating a recombinant construct, 2) dephosphorylation of dNTPs after PCR amplifications, occasionally in combined use with a single-strand exonuclease that hydrolyses primers to dNTPs, to omit the need of further clean-up before direct DNA sequencing of PCR products or SNP genotyping, or 3) dephosphorylation of DNA ends for subsequent labeling with $^{32}P$ using $[\gamma\text{-}^{32}P]NTP$ and T4 polynucleotide kinase. The aforementioned alkaline phosphatase reactions are intermediate steps in typical DNA analysis processes. Alkaline phosphatases are also commonly used in reporter systems, such as in enzyme-linked immunosorbent assays (ELISA), in gene-fusion or gene-delivery systems, or in conjugation to oligonucleotides used as hybridization probes.

At least three alkaline phosphatase enzymes are commercially available and commonly used in molecular biology applications, including: i) calf intestinal alkaline phosphatase (CIP), ii) shrimp alkaline phosphatase (SAP) from the arctic shrimp *Pandalus borealis*, and iii) bacterial alkaline phosphatase (BAP), isolated from *Escherichia coli*. Bacterial Alkaline Phosphatase dephosphorylates all types of DNA ends but is difficult to inactivate because it is very resistant to heat and detergents. (See, Sambrook et al., Molecular Cloning, A Laboratory Manual, §1.53-1.72, 1989). CIP is also widely used in molecular biology techniques (for instance, see U.S. Pat. Nos. 5,773,226 and 5,707,853) but requires the use of Proteinase K treatment followed by phenol:chloroform extractions, or a heat step followed by phenol:chloroform extractions, to remove the enzyme when the reaction is completed.

A genetically engineered temperature sensitive BAP mutant has been reported. (See, Shandilya et al., 1995, *Focus*, 17(3):93-95). This mutant enzyme (TsAP), sold by LifeTechnologies, Inc., is inactivated (95% or more) by heat (65° C. for 15 minutes) in the presence of EDTA.

Psychrophiles, or cryophiles, are extremophilic organisms that are capable of growth and reproduction in cold temperatures. In recent years, thermolabile alkaline phosphatases have been developed. Among them is the heat labile phosphatase from the psychrophilic strain TAB5 which was discovered in Antarctica and is referred to as Thermolabile Antarctic phosphatase (TAP). (See, Rina et al., *Eur. J. Biochem.* 267:1230-1238, 2000, and U.S. Pat. No. 7,319,014). TAP is heat labile and has a high specific activity; but does not possess significant dephosphorylation activity of dNTPs after PCR amplification.

A psychrophilic alkaline phosphatase (PAP), developed in Japan and isolated from the *Shewanella* sp. SIB 1 has been reported and is a cold-active alkaline phosphatase. (See, Japanese Patent No. 2001-172653). It has been reported that PAP has high specific activity at low temperature (Ishida et al., 1998, *Biosci. Biotechnol. Biochem.*, 62, 2246-2250). It is not known whether PAP is active in dephosphorylating dNTPs after PCR amplification.

Two additional heat-labile alkaline phosphatases from a psychrophilic microorganism have been purified and characterized. (See, de Prada et al., 1997, *Appl. Env. Microbiol.*, 63(7): 2928-2931). However, no specific activity (units/mg protein) and no primary structures have been reported for these enzymes.

A second cold-adapted alkaline phosphatase, this one from atlantic cod, was isolated and characterized. (See, Asgeirsson et al., 1995, *Comp. Biochem. Physiol.*, 110B(2): 315-329). The cod alkaline phosphatase exhibited thermolability similar to SAP. No primary structure of the protein/gene has been provided. Further, trout fish alkaline phosphatase isozymes have been isolated. (See, Whitmore et al., 1972, *J. Exp. Zool.*, 182: 59-68). Additionally, shrimp from the warm water region near Taiwan express several alkaline phosphatases. (See, Lee et al., 1991, *Comp. Biochem. Physiol.*, 99B(4): 845-850).

SAP, isolated from the arctic shrimp *Pandalus borealis*, was found in the processing wastewater from the shrimp industry. (See, Olsen et al., 1990, *Process Biochem.*, 25:67-68). This enzyme was later identified as originating from shrimp hepatopancreas. (See, Olsen et al., 1991, *Comp. Biochem. Physiol.*, 99B(4):755-761). This alkaline phosphatase possesses maximum enzyme activity at about 40° C., whereas CIP possesses maximal activity at about 45° C. Although the temperature for maximum activity is close to 40° C., SAP looses activity when pre-incubated for a period of 15 minutes at temperatures above 37° C. SAP has been reported to loose 95% of activity if pre-incubated at 65° C. for 15 minutes. In comparison, after similar heat-treatments, CIP retains 40% activity.

As noted above, commercial SAP is obtained from wastewater generated by the shrimp industry. Freshly collected shrimp are first frozen in large blocks. Then, the frozen shrimp are thawed by re-circulated cold water. During the process of freezing and thawing, the hepatopancreas of the shrimp are ruptured and the contents thereof are released into the circulating water. This wastewater is then concentrated and several protein purification steps are employed to purify SAP.

SAP is frequently used to dephosphorylate cloning vectors prior to ligation reactions, and to treat PCR amplification product-mixtures prior to DNA sequencing reactions, as described in U.S. Pat. Nos. 5,741,676, 5,756,285, 6,379,940 and 6,387,634.

Production efficiency of SAP suffers from varying quality of the wastewater. Variation in the yield quality of SAP from this natural source stems mainly from the natural seasonal variation of enzyme production in the shrimp, handling of the shrimp source prior to or during freezing, and handling of the shrimp or water during or after the thawing process. Further, there is growing concern about the future availability of shrimp collection wastewater. As a natural resource, shrimp may be depleted through over-fishing or other acts of nature. Changes in the shrimp industry, i.e. single-freezing, and processing of the shrimp, may also eliminate the wastewater source. (See, U.S. Pat. No. 7,323,325).

Thus, there is a demand for a recombinant SAP product which is sustainable. Recombinant products may be preferred in molecular biology applications where product purity is important, e.g. in the production of DNA based therapeutics or in forensic science, and where strict standardization is required. There is therefore a desire in the field for a synthetic or recombinant source of alkaline phosphatase which is produced in a uniform and pure fashion.

Recently, a recombinant SAP has been developed. (See, U.S. Pat. No. 7,323,325). However, recombinant SAP is not presently commercially available.

The molecular biology field, as well as other similar fields using alkaline phosphatases, would significantly benefit from a source of isolated, high-quality, recombinant heat labile alkaline phosphatase enzyme. However, such commercial availability encompassing all of these attributes is as yet unrealized.

Psychrophilic organisms have successfully adapted to various low temperature environments such as cold ocean waters. Thermal compensation of cold adapted enzymes found in such organisms is realized through improved turnover number and catalytic efficiency, and a highly flexible structure. (See, Feller et al., *Cell. Mol. Life. Sci.*, 53:830-841, 1997). In such environments, organisms produce enzymes with increased catalytic efficiencies, generally at the expense of thermal stability due to fewer non-covalent stabilizing interactions. (See, Hauksson et al., *Enzym. Micrbiol. Tech.*, 27:66-73, 2000).

*Colwellia psychrerythraea* is a non-pathogenic, obligate psychrophile and Gram-negative bacteria. *C. psychrerythraea* is a member of the proteobacteria phylum, class gammaproteobacteria. This bacterium is rod-shaped, red in pigment, possesses flagella and can be found in cold marine environments such as the Arctic and Antarctic sea ice. Strain 34H, in particular, was isolated from Arctic marine sediments. Strain 34H of *C. psychrerythraea* has a growth temperature range of from −1° C. to 10° C. Optimal growth appears at 8° C., with maximum cell yield occurring at the subzero temperature of −1° C. Cells are able to survive in temperatures as low as −10° C. Growth can occur under deep sea pressure as well.

Alkaline phosphatases are in general difficult to express in *E. coli* and heat labile family members tend to present an even greater challenge due to their low thermal stability. Many problems may occur during expression of the protein and many hurdles typically present themselves to obtaining purified, active protein. One problem is that expressed protein may be abundant, but inactive, i.e. expressed but conglomerated in unusable inclusion bodies in the bacterial host. The degree of inactivity of isolated recombinant protein may be related to growth conditions (growth and induction temperature, media composition, induction time).

An expression system, media composition and growth conditions are disclosed herein which are capable of yielding sufficient quantities of active recombinant *C. psychrerythraea* heat labile alkaline phosphatase (CAP). The present methods enable production of sufficient quantities of CAP protein to be commercialized, as described in general, below. Disclosed are methods of over-expression and purification of the recombinant alkaline phosphatase and mutants thereof. Particularly, disclosed are methods of over-expressing and purifying commercially useful quantities of active recombinant heat labile alkaline phosphatase fusion enzymes from *C. psychrerythraea*, wherein the fusion enzymes comprise one or more heterologous sequences. The disclosed *C. psychrerythraea* heat labile alkaline phosphatase has properties similar to shrimp alkaline phosphatase and can be substituted for shrimp alkaline phosphatase in assays involving the same.

SUMMARY OF THE INVENTION

Isolated nucleic acids comprising: a) the sequence according to SEQ ID NO:3; b) the sequence which is at least 95% identical to SEQ ID NO:3; c) the sequence which is fully complementary to SEQ ID NO:3; d) the sequence which is fully complementary to the sequence which is at least 95% identical to SEQ ID NO:3; or e) the sequence which hybridizes to SEQ ID NO:3 under stringent conditions, wherein the isolated nucleic acid sequence further comprises fused thereto a nucleic acid sequence encoding a hydrophilic repeating polypeptide sequence, wherein the hydrophilic repeating polypeptide sequence may comprise, but is not limited to, for instance, one, two, three, or more repeats of the dipeptide HQ, isolated vectors comprising the same and isolated bacterial hosts comprising the isolated vectors. The sequences encode fusion proteins comprising polypeptide sequences of heat labile alkaline phosphatases from the genome of *C. psychrerythraea*, fused to a heterologous sequence, referred to hereinbelow as an HQ fusion sequence, which may comprise, but is not limited to, for instance, one, two, three or more repeats of the dipeptide HQ.

Provided is an isolated recombinant protein comprising the sequence according to SEQ ID NO:15, or a sequence at least 95% identical to SEQ ID NO:15. The protein additionally comprises a hydrophilic repeating fusion polypeptide sequence, which may comprise, but is not limited to, for instance, one, two, three, or more repeats of the dipeptide HQ.

Also provided are methods of dephosphorylating nucleotides and other substrates of alkaline phosphatase enzymes, which comprises incubating the substrate with the isolated recombinant proteins of disclosed herein. Additionally, methods are disclosed including incubation of the substrates with the isolated enzymes with an exonuclease prior to direct DNA sequencing. Other methods disclosed herein include methods that may be performed immediately following termination of a polymerase chain reaction, and wherein the nucleotide is an unused substrate of the polymerase chain reaction. Further, disclosed are methods which further include labeling dephosphorylated products from such incubation steps with $^{32}$P by further incubation with [γ-$^{32}$P]NTP and an effective amount of T4 polynucleotide kinase.

Kits including the isolated proteins according to the disclosed methods and compositions are also contemplated.

Finally, disclosed are isolated nucleic acids having sequences which include: a) the genomic heat labile alkaline phosphatase sequences from *C. psychrerythraea*, wherein the sequences are fused to the nucleic acid sequence encoding a hydrophilic repeating polypeptide sequence, wherein the heterologous polypeptide sequence may be from one to ten repeating units of the polypeptide sequence HQ, b) sequences which are at least 95% identical to the sequences of a); c) sequences which are fully complementary to the sequences of a); d) sequences which are fully complementary to the sequences which are at least 95% identical to the sequences of a); and e) sequences which hybridize to the sequences of a) under stringent conditions. The hydrophilic repeating polypeptide sequences may be fused alternatively either upstream or downstream of the aforementioned sequences.

BRIEF DESCRIPTION OF THE DRAWINGS

FIG. 2. *Colwellia psychrerythraea* 34H GenBank ID 3519034 alkaline phosphatase (A) nucleic acid sequence, and (B) protein sequence.

DETAILED DESCRIPTION OF THE INVENTION

Figure 1:
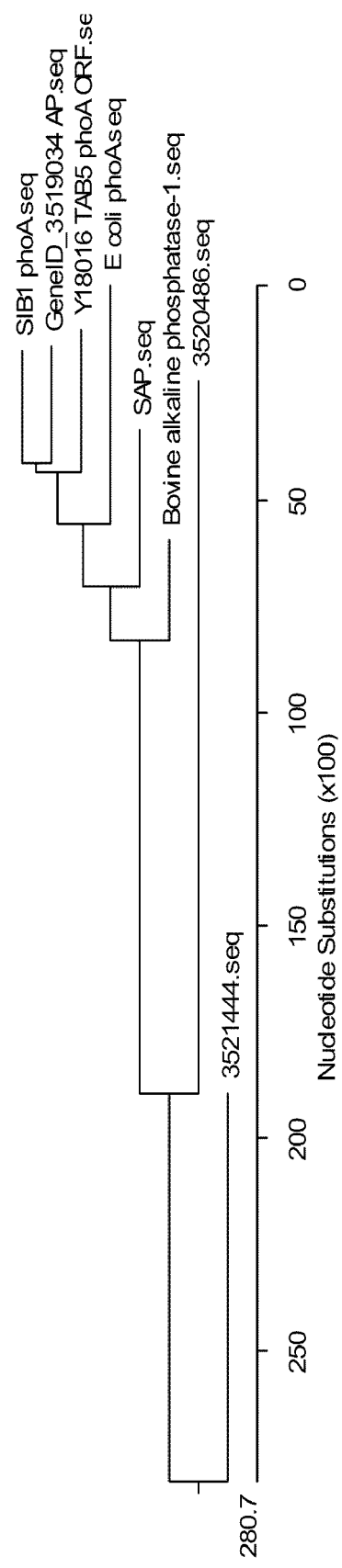
FIG. 1. Phylogenetic analysis of *C. psychrerythraea* putative alkaline phosphatase nucleotide sequences. The nucleotide sequences (DNA) were obtained from GenBank and analyzed using MegAlign software.

Reference will now be made in detail to exemplary embodiments. While the disclosed methods and compositions will be described in conjunction with the exemplary embodiments, it will be understood that they are not intended to limit the discloses methods and compositions to these embodiments. On the contrary, the application is intended to encompass alternatives, modifications and equivalents, which may be included within the spirit and scope of the present disclosure.

Disclosed are many preferred embodiments which rely on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

Throughout this disclosure, various aspects of the disclosed methods and compositions can be presented in a range format. It should be understood that the description in range format is merely for convenience and brevity and should not be construed as an inflexible limitation on the scope of the disclosed methods and compositions. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The present methods and compositions may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques are provided in the examples hereinbelow. However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, *Principles of Biochemistry* 3$^{rd}$ Ed., W.H. Freeman Pub., New York, N.Y. and Berg et al. (2002) *Biochemistry*, 5$^{th}$ Ed., W.H. Freeman Pub., New York, N.Y., all of which are herein incorporated in their entirety by reference for all purposes.

The term "effective amount" as used herein refers to an amount sufficient to induce a desired result.

The term "hybridization" as used herein refers to the process in which two single-stranded polynucleotides bind noncovalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1 M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" 2$^{nd}$ Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., Science 254, 1497-1500 (1991), and other nucleic acid analogs and nucleic acid mimetics.

The term "hybridizing specifically to" as used herein refers to the binding, duplexing, or hybridizing of a molecule only to a particular nucleotide sequence or sequences under stringent conditions when that sequence is present in a complex mixture (for example, total cellular) DNA or RNA.

The term "isolated nucleic acid" as used herein means an object species that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

The term "nucleic acids" as used herein may include any polymer or oligomer of pyrimidine and purine bases, preferably cytosine, thymine, and uracil, and adenine and guanine, respectively. (See, Albert L. Lehninger, PRINCIPLES OF BIOCHEMISTRY, at 793-800, Worth Pub. 1982). Indeed, contemplated are deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides disclosed herein may include sequences of deoxyribonucleic acid (DNA) or ribonucleic acid (RNA) which may be isolated from natural sources, recombinantly produced or artificially synthesized and mimetics thereof. A further example of a polynucleotide disclosed herein may be peptide nucleic acid (PNA). Also contemplated and encompassed are situations in which there is a nontraditional base pairing such as Hoogsteen base pairing which has been identified in certain tRNA molecules and postulated to exist in a triple helix. "Polynucleotide" and "oligonucleotide" are used interchangeably in this application. The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

As used herein, "comprising," "including," "containing," "characterized by," and grammatical equivalents thereof are inclusive or open-ended terms that do not exclude additional, unrecited elements or method steps, but also includes the more restrictive terms "consisting of" and "consisting essentially of."

Ready sources of large quantities of recombinant heat labile alkaline phosphatase has been lacking despite a need for such sources. The enzymatic activity of alkaline phosphatase is utilized in many different molecular biology assays and reactions. To date, the majority of heat labile alkaline phosphatase has been obtained from natural sources. With the potential for these sources to be depleted either by over-consumption or change in processing technology in the fishing industry, it is highly desirable to find an inexhaustible supply of proteins possessing this extremely useful activity.

To this end, the present inventors cloned and sequenced heat labile alkaline phosphatase enzymes from different sources that may be used for producing the enzymes recombinantly. A heat labile alkaline phosphatase from the cold adapted marine Gram-negative bacterium *Colwellia psychrerythraea* 34H has been cloned and sequenced. However, as is commonly experienced with enzymes from psychrophilic bacteria, attempts at expressing the recombinant enzyme in *E. coli* using standard transfection and induction methods were inefficient or resulted in lower yields. (See, Miroux and Walker, *J. Mol. Biol.*, 1996, 260(3):289-298, for typical recombinant protein expression techniques). Poor yields and inactive enzyme are commonly obtained when attempting these techniques with alkaline phosphatases.

Several alternative constructs of CAP were tested, including deletions, substitutions and additions, all in attempts to obtain large quantities of active recombinant CAP. For instance, full-length CAP was tested, including signal sequence. Removal of the sequence was also tested, e.g. deletion of the amino-terminal 17 amino acids. Other deletion mutations up to and including deletion of the amino-terminal 1-39 amino acids were examined in an effort to find a sequence which would produce large quantities of active protein. Other signal peptides were added to CAP in an effort to enhance yield, such as leader sequences from YebF and BAP. None of these investigations yielded the desired result of large quantities of active CAP enzyme. An alternative form of alkaline phosphatase was found that enabled isolation of abundant quantites of active CAP enzyme in *E. coli* using conventional expression vectors.

It was found that addition of a hydrophilic stretch of amino acids at the carboxy-terminus of CAP enabled production of large quantities of active enzyme which were isolatable using conventional protein purification techniques. Addition of a stretch of as many as six hydrophilic amino acids, including the sequence HQHQHQ (SEQ ID NO:4, corresponding to nucleic acid sequence SEQ ID NO:16), appeared to be helpful in obtaining functional enzyme. Thus, in one embodiment, a CAP fusion protein containing the sequence HQHQHQ (SEQ ID NO:4, corresponding to nucleic acid sequence SEQ ID NO:16) at its carboxy-terminus is disclosed.

In another embodiment, the fusion sequence of HQHQHQ, hereinafter referred to as the HQ fusion sequence, may include as few as one repeat of the sequence HQ, and as many as ten or more repeats of the sequence HQ. Thus, in one embodiment, the HQ fusion sequence may comprise the sequence HQHQHQHQHQHQHQHQHQHQ (SEQ ID NO:8) and nucleic acids encoding the sequence, fused to the carboxy-terminus or amino-terminus, or both, of a desired protein. Other embodiments encompasses HQ fusion sequences which include a single repeat of HQ, two repeats (HQHQ), three repeats (HQHQHQ, SEQ ID NO:4), four repeats (HQHQHQHQ, SEQ ID NO:9), five repeats (HQHQHQHQHQ, SEQ ID NO:10), six repeats (HQHQHQHQHQHQ, SEQ ID NO:11), seven repeats (HQHQHQHQHQHQHQ, SEQ ID NO:12), eight repeats (HQHQHQHQHQHQHQHQ, SEQ ID NO:13) and even as many as nine repeats (HQHQHQHQHQHQHQHQHQ, SEQ ID NO:14), or more are disclosed, and/or nucleic acid sequences encoding the same, which are fused to the carboxy-terminus and/or the amino-terminus of a desired protein.

In another embodiment, the HQ fusion sequence may be fused to either the carboxy-terminus or the amino-terminus, or both, of the desired protein of interest. That is, the HQ fusion sequence may be fused at either terminus of any protein to be expressed and purified, preferably in active form and in large quantities, in a recombinant protein expression system. Other alkaline phosphatases (EC 3.1.3.1) are encompassed by this embodiment, from other organisms, as well as, but not limited to, proteins related to the general family of phosphatases, such as serine and threonine phosphatases, tyrosine phosphatases, histidine phosphatases, lipid phosphatases, etc.

In another embodiment, the HQ fusion sequence may also be added to either terminus of proteins unrelated to phosphatases, such as, but not limited to, other prokaryotic proteins (bacterial and archaeal) as well as other eukaryotic proteins.

The recombinant heat-labile alkaline phosphatase from *C. psychrerythraea* was purified and its enzymatic properties were compared with those of SAP, such as substrate specificity, specific activity, heat-lability, and performance with ExoI prior to sequencing reactions. The results obtained reveal that *C. psychrerythraea* alkaline phosphatase has comparable activity to that of SAP.

More particularly, three *C. psychrerythraea* genes, GenBank ID Nos. 3521444 (SEQ ID NO:1), 3520486 (SEQ ID NO:2) and 3519034 (SEQ ID NO:3), were identified by GenBank as alkaline phosphatases based on aligned amino acid sequences. The three gene sequences were compared to other psychrophilic and mesophilic alkaline phosphatase enzymes. The phylogenetic tree, depicted in FIG. 1, shows the evolutionary relationships among various biological species. From FIG. 1, it is readily apparent that ID 3519034 is the closest sequence related to the psychrophilic TAB5 and SIB1 alkaline phosphatases as well as the shrimp alkaline phosphatase sequence. The nucleic acid and protein sequences of GenBank ID No. 3519034 are depicted in FIG. 2. All sequence for GenBank Nos. 3521444, 3520486 and 3519034, and their corresponding amino acid sequences, are hereby incorporated by reference in their entirety.

The sequence of GenBank ID 3519034 encodes a heat labile alkaline phosphatase. This nucleic acid molecule was amplified by Polymerase Chain Reaction (PCR) and cloned into various expression vectors. It was later found that addition of a fusion peptide comprising three pairs of histidine-glutamine amino-acid residues, at the 3' terminus, dramatically improves expression protein and yield of active protein.

Particularly, some embodiments encompass the sequence of heat labile alkaline phosphatase from *C. psychrerythraea*, such as any one of GenBank ID Nos. 3521444 (SEQ ID NO:1), 3520486 (SEQ ID NO:2) and 3519034 (SEQ ID NO:3), further containing as a fusion one or more of the aforementioned HQ fusion sequences, or nucleic acids encoding the same, fused to either terminus of the protein, for instance, a six amino-acid sequence fused to the carboxy-terminus which comprises the sequence HQHQHQ (SEQ ID NO:4, corresponding to nucleic acid sequence SEQ ID NO:16).

More particularly, encompassed and contemplated are the sequence of GenBank ID No. 3519034 (SEQ ID NO:3) fused at its carboxy-terminus with the sequence encoding HQHQHQ (SEQ ID NO:16), which is represented herein as polypeptide sequence SEQ ID NO:5, and sequences complementary thereto, as well as sequences hybridizing thereto under stringent conditions.

In another embodiment, the HQ fusion sequence may be any one or more of the HQ fusion sequences discussed above, such as any one of SEQ ID NOS: 8-14. In yet another embodiment, the CAP enzyme genes encompassed herein include those alkaline phosphatase enzyme genes, i.e. SEQ ID NOs: 1-3, further comprising one or more nucleic acid sequences which encode the aforementioned HQ fusion sequences, resulting in a fusion protein in which the HQ fusion sequence is fused to either the carboxy-terminus of the CAP enzymes or amino-terminus of the CAP enzymes, as well as sequences which are at least 90%, at least 91%, at least 92%, at least 93%, at least 94%, at least 95%, or 100% identical thereto, sequences complementary to the nucleic acid sequences thereof, sequences hybridizing thereto under stringent conditions, and all possible polypeptides obtained from translation and expression of these CAP enzyme gene sequences.

In another embodiment, vectors and other plasmids which comprise the above-described sequences are disclosed. That is, the insertion of the above-mentioned sequences into conventional cloning and expression vectors, as well as shuttle vectors and the like are contemplated and disclosed. For instance, the fusion protein SEQ ID NO:5 may be cloned into a cloning vector, expression vector or other shuttle vector for the purposes of expression and purification, sequencing or other analysis. The embodiments disclosed herein encompass these variations of the above-described sequences. The vectors may include an operably linked promoter, enhancer, or other genetic elements.

The recombinant expression vector or expression plasmid comprising the nucleic acid molecule encoding for the *C. psychrerythraea* heat labile alkaline phosphatase may be grown in a prokaryotic host cell. Any number of conventional prokaryotic host cells may be employed in amplifying and expressing the nucleic acids disclosed herein. In another embodiment, the above-identified sequences, cloned into a vector, such as a cloning vector or expression vector, may be transfected into one or more prokaryotic cells, yeast cells, baculoviral cells, or mammalian cells. Therefore, embodiments disclosed herein encompass those cells harboring the aforementioned and described sequences containing HQ fusion sequences.

Recombinant cells of *E. coli* comprising the nucleic acid molecule encoding for the *C. psychrerythraea* heat labile alkaline phosphatase were isolated according to standard procedures. Polypeptide corresponding to the *C. psychrerythraea* heat labile alkaline phosphatase fusion protein was recovered using conventional protein purification techniques, as described in more detail below. Thus, other embodiments disclosed encompass cells and cell extracts comprising the proteins discussed above containing the HQ fusion sequences. These include extracts, solutions of protein obtained from intermediate steps in purification which comprise the sequences containing the HQ fusion sequences, and pure or substantially pure proteins, such as, but not limited to, pure or substantially pure recombinant heat labile alkaline phosphatase which contains the HQ fusion sequence of HQHQHQ (SEQ ID NO:4, corresponding to nucleic acid SEQ ID NO:16) fused to the carboxy-terminus as in SEQ ID NO:5.

It was found that the recombinant *C. psychrerythraea* alkaline phosphatase is capable of dephosphorylating dNTPs in the presence of ExoI after PCR amplification, prior to sequencing. It was further found that the presently disclosed recombinant *C. psychrerythraea* alkaline phosphatase is heat inactivated under substantially the same conditions as SAP.

In another embodiment, the CAP-fusion protein, comprising the HQ fusion sequence at its carboxy-terminus, is employed any number of molecular biology-based assays. One of skill in the art will immediately understand that the present enzymes may be used in any similar assay for which heat labile alkaline phosphatases, or phosphatases in general, are typically used in molecular biology, biochemistry, genetics and such. The following are a few non-limiting examples for which the present enzymes may be utilized. For instance, the enzymes encompassed by the various embodiments disclosed herein may be employed to dephosphorylate vector DNA after restriction enzyme digestion to minimize self-ligation of the cloning vector, thus favoring ligation of the insert to the vector and creating a recombinant construct. In another embodiment, the enzymes disclosed herein may be employed to dephosphorylate dNTPs after PCR amplifications. In a further embodiment, the present enzymes may be employed in combined use with a single-strand exonuclease that hydrolyses primers to dNTPs, to omit the need of further clean-up before direct DNA sequencing of PCR products. In a further embodiment, the present enzymes may be employed to dephosphorylate DNA ends for subsequent labeling with $^{32}P$ using $[\gamma\text{-}^{32}P]NTP$ and T4 polynucleotide kinase. In yet another embodiment, the present enzymes may be employed in any number of known reporter systems, such as in enzyme-linked immunosorbent assays (ELISA), in gene-fusion or gene-delivery systems, or in conjugation to oligonucleotides used as hybridization probes.

The following list of examples is provided for illustrative purposes only. While the present disclosure is intended to encompass these examples, it will be clear to one of skill in the art that these are non-limiting examples and that many modifications may be made to the examples while still maintaining subject matter within the scope of the application. Therefore, these examples are non-limiting examples.

EXAMPLES

Example 1

Cloning of *C. psychrerythraea* Alkaline Phosphatase

*C. psychrerythraea* genomic DNA was purchased from ATCC (#BAA-681D) and was used as a template to amplify the alkaline phosphatase sequence GenBank ID 3519034 (CAP). For the amplification, a forward primer containing an NdeI restriction site (underlined) with *E. coli* codon optimization (lower case) had the following sequence (SEQ ID NO:6):

```
5'- ATC CATATG AAA AAA CTg CTg TCC GCC G-3'
```

The reverse primer containing a SmaI restriction site (underlined) including the codons of a His/Gln tag (bold) had the following sequence (SEQ ID NO:7):

```
5'-CG CCC GGG CTA CTG ATG TTG ATG TTG ATG CTT
TTT ACC TAG TAA AGT-3'
```

PCR was performed using an MJ Research PT-200 thermal cycler and the FideliTaq™ PCR Master Mix (USB Corp.). The amplified DNA fragment was isolated by agarose gel electrophoresis, gel purified, using PrepEase® Gel Extraction Kits (USB Corp.) and ligated into the TOPOII vector (Invitrogen cat# K2800), transformed into TOP10 chemically competent *E. coli* (Invitrogen) and the resulting plasmid containing the CAP gene was selected in the presence of kanamycin. The clone bearing the CAP gene was sequenced and found to be free of mutations.

The plasmid was then digested with NdeI and SmaI restriction enzymes (NEB) and inserted into the pET17b vector (Novagen) previously digested with NdeI and EcoRV (NEB), although it will be recognized by one of skill in the art that other equivalent expression vectors may be used for the same purpose. That is, other expression vectors were also tested with similar results, including such vectors as pET14b, pRE and pUC19. The pET17b expression vector is under the control of the T7 promoter and the transcription is induced with isopropyl β-D-thiogalactopyranoside (IPTG). The resulting plasmid containing CAP gene was selected in the presence of ampicillin.

Example 2

Growth and Expression of *C. psychrerythraea* Alkaline Phosphatase

The pET17b plasmid containing the CAP gene under the control of T7 promoter was grown overnight at 37° C. in 4 liters Terrific Broth and 100 µg/ml ampicillin. This culture was used to inoculate 55 liters of TB and 100 µg/ml ampicillin in the New Brunswick fermentor. The cells were incubated with aeration at 30° C. At a cell density corresponding to $A_{600}=2.7$, the cofactors 10 mM $MgCl_2$ and 80 µM $ZnCl_2$ were added to the culture medium and the cells were induced by adding 1 mM IPTG. After induction, the cells were incubated at 20° C. for 24 hours and then harvest by centrifugation at 10,000 rpm in a Cepa centrifuge. The cell paste (900 g) was then stored at −80° C.

Example 3

Purification of Active Recombinant *C. psychrerythraea* Alkaline Phosphatase

It should be noted that many different strains of bacteria are available for the purpose of expressing and purifying recombinant proteins. Several of these were empirically evaluated.

Furthermore, different mutations, including substitutions, deletions and additions, of the CAP protein were tested in various expression vectors and in different bacterial strains. Fusions proteins were constructed using leader peptides from other alkaline phosphatases and *E. coli* proteins. These genetic constructs were all tested in different expression vectors and bacterial host. The general protocols listed above were used for all mutations examined.

As is known in the art, alkaline phosphatases are in general difficult to express in *E. coli* and heat labile versions present an even greater challenge due to their low thermal stability. Many problems may occur during expression of the protein and many hurdles typically present themselves to obtaining purified, active protein. One problem is that expressed protein may be abundant, but inactive. The degree of inactivity may be related to growth conditions (growth and induction temperature, media composition, induction time). An expression system, media composition and a growth condition was discovered which was capable of yielding enough CAP active protein to be commercialized, as described in general, below.

For instance, it was noted that more activity was realized when a peptide was attached to the protein at the C-terminus. Although not wishing to be bound by any specific theory, teleologically, it may be that the peptide helps the folding and/or the solubility and/or the stability of the protein in the cytoplasm. Enzyme is secreted in the periplasm where the pro-enzyme is cleaved from its signal peptide. To be able to cross the periplasmic membrane, the enzyme has to be soluble. Further, divalent cations (such as magnesium and zinc) are required to be added to the growth media for CAP to be active. In the absence of these two divalent cations, the protein is less soluble and less enzyme is transported through the membrane. Again, without wishing to be bound by any specific theory, it is possible that the cations Mg and Zn play a role in the stability/solubility of the protein in the cytoplasm.

Therefore, the following exemplary purification scheme is a general purification protocol which may provide satisfactory quantities of active recombinant CAP. Variations of this general strategy may be made by one of skill in the art without substantially departing from the present methods and compositions. As one of skill in the art knows, there are often multiple manners in which a protein may be purified. Thus, the following is one example of the many possible protocols which may be successfully employed to isolate the recombinant protein.

Preparation of cell extract—60 g of frozen cells were thawed in 200 ml of 30 mM Tris-HCl pH 9.0, 1 mM MgCl$_2$, 10% glycerol, 30 mM NaCl, 3% Deoxycholate (DOC) and 20 ml of lysozyme (10 mg/ml) was added. After incubation of the mixture for 30 minutes on ice with constant stirring, the cells were sonicated to translucency. The lysate was then centrifuged for 45 min at 40,000 rpm in a Beckman Ti-45 rotor. The supernatant (220 ml) was Fraction I.

DEAE Cellulose chromatography—A column of Whatman DE52 DEAE cellulose (19.6 cm$^2$×5 cm) was prepared and equilibrated with 30 mM Tris-pH 9.0, 1 mM MgCl$_2$, 10% glycerol, 30 mM NaCl, 0.25% TritonX-100 (Buffer A). Fraction I was diluted with Buffer A to give a conductivity equivalent to buffer A. The diluted Fraction I (~350 ml) was applied to the column. CAP is not retained under these conditions. The flow through and wash fractions (~400 ml) were pooled to give fraction II.

Heparin Sepharose CL-6B Chromatography—A column of Heparin (5.3 cm$^2$×7 cm) was prepared and equilibrated with buffer A. Fraction II was applied to the column and eluted with a linear gradient from 30 mM to 1M NaCl. The fractions were analyzed on SDS Page and the fractions (76 ml) containing the CAP were pooled and dialyzed overnight against 10 mM MES-pH 6.5, 1 mM MgCl$_2$, 10% glycerol, 30 mM NaCl, 0.25% TritonX-100 (Buffer B) (Fraction III).

SP Sepharose Fast Flow Chromatography—A column of SP Sepharose fast flow (5.3 cm$^2$×12 cm) was prepared and equilibrated with Buffer B. Fraction III was applied to the column and eluted with a linear gradient from 30 mM to 1M NaCl. The fractions were analyzed on SDS Page and the fractions (88 ml) containing the CAP were pooled and dialyzed overnight against Buffer B again (Fraction IV).

P-cell—A column of P-cell (19.6 cm$^2$×8 cm) was prepared and equilibrated with Buffer B. Fraction IV was applied to the column and eluted with a linear gradient from 30 mM to 1M NaCl. The fractions containing CAP appear to be homogeneous as a single band judged by electrophoresis under denaturing conditions, but exonuclease contaminant assay showed some level of exonuclease activity. The fractions (64 ml) containing the CAP were pooled and dialyzed overnight against Buffer A (Fraction V).

Q Sepharose HiTrapQ Chromatography—To remove the contaminating exonuclease activity, fraction V was applied to HighTrapQ. CAP is not retained under these conditions and flows through the column but the exonuclease contaminants are retained under these conditions. The flow through containing the CAP protein was analyzed for contaminants and did not show any detectable level of exonuclease activity. (Fraction VI)

SP Sepharose Fast Flow Chromatography—To concentrate the CAP protein, a column of SP Sepharose fast flow (2 cm$^2$×2.5 cm) was prepared and equilibrated with Buffer B. Fraction VI was applied to the column and eluted with a step gradient from 30 mM to 850 mM NaCl. Unfortunately the fraction collector did not work properly and some protein got lost. What was recovered (8 ml) was analyzed for the presence of CAP on SDS Page and dialyzed against 25 mM Tris pH7.5; 1 mM MgCl$_2$, 0.1 mM ZnCl$_2$; 50% glycerol (Final Buffer) and stored at −20° C. (Fraction VII) (2 ml)

Protein Concentration—Purity—The protein concentration was determined using the BCA Protein Determination Assay against a BSA standard curve and was 1.69 mg/ml. After electrophoresis of the purified CAP protein under denaturing conditions, staining with Coomassie Blue produced a single band corresponding to a molecular weight of approximatively 50,000. Even though the molecular weight of the predicted mature CAP protein is 50,710 Da, in SDS-PAGE analysis, recombinant CAP migrates as a single band at about 50,000 Da.

Example 4

Characterization of Recombinant *C. psychrerythraea* Alkaline Phosphatase

*C. psychrerythraea* alkaline phosphatase was purified to homogeneity from 60 gm of cells and characterization was performed on this purified batch. Activity of the phosphatase was determined based on the amount of alkaline phosphatase that hydrolyzes 1 μmol of p-nitrophenyl phosphate (synthetic substrate) per min at 37° C. at pH 10.4. Thus, 1 unit of enzyme activity is the amount of enzyme which catalyzes the hydrolysis of 1 μmol of p-nitrophenyl phosphate per minute in glycine buffer (pH 10.4) at 37° C. Reaction mixtures contain 100 mM glycine (pH 10.4), 1.0 mM MgCl$_2$, 1.0 mM ZnCl$_2$, 10 mM p-nitrophenyl phosphate and 0.001-0.01 units of alkaline phosphatase.

Example 5

Heat Inactivation of Recombinant *C. psychrerythraea* Alkaline Phosphatase at 65° C.

Figure 3:
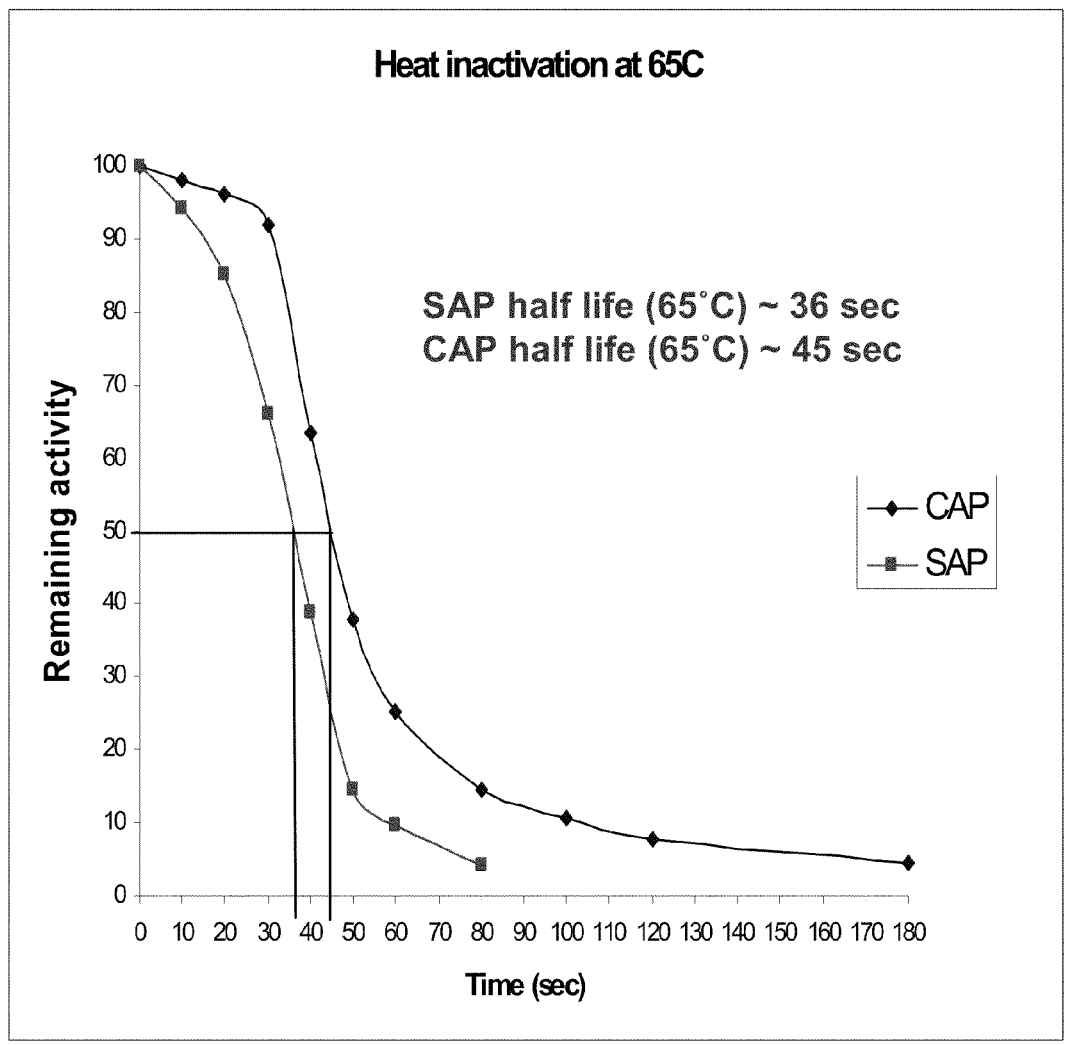
FIG. 3. Heat-inactivation of *Colwellia psychrerythraea* Alkaline Phosphatase and Shrimp Alkaline Phosphatase at 65° C. SAP and CAP were diluted to 0.01 U/μl in 20 mM Tris pH 7.5; 1 mM MgCl$_2$; 0.1 mM ZnCl$_2$. 20 μl aliquots were incubated at 65° C. for increasing periods of time. 10 μl was used for an activity assay in a 2 ml reaction volume.

Heat-inactivation data were obtained at 65° C. using CAP, compared in parallel to Shrimp Alkaline Phosphatase (SAP). In general, 20 μl of 0.01 U/μl CAP and SAP were diluted in Dilution Buffer (20 mM Tris pH 7.5; 1 mM MgCl$_2$; 0.1 mM ZnCl$_2$) and were incubated at 65° C. for the indicated periods of time. From the incubation, 10 μl was immediately extracted and assayed for remaining phosphatase activity by addition to in 2 ml of reaction buffer (150 mM Glycine-NaOH pH 10.4; 1.5 mM MgCl$_2$; 1.5 mM ZnCl$_2$; 18 mM para-Nitrophenylphosphate (pNPP)). Exemplary results are shown in Table 1 and depicted in FIG. 3.

TABLE 1

| Enzyme | Half life (65° C.) |
| --- | --- |
| *Colwellia* AP | 45 sec |
| Shrimp AP | 36 sec |

Recombinant CAP heat inactivation at 65° C. was similar to SAP heat inactivation at the same temperature. It was found that the recombinant CAP is heat labile and is 95% inactivated after 180 seconds at 65° C.

Example 6

Activity of Recombinant *C. psychrerythraea* Alkaline Phosphatase Using dATP as Substrate Activity of CAP using deoxyadenosine-5'-triphosphate (dATP) as a substrate was performed by incubating 10 nmol dATP spiked with 5 μCi $^{33}$P-α-dATP (1.66 pmol) in 10 mM Tris pH 8.6, 50 mM KCl, 1.5 mM MgCl$_2$ (PCR buffer) with 0.4 unit of enzyme in a 10 μl reaction volume for the indicated intervals at 37° C. As a control, 0.4 unit of SAP was tested using the same conditions. 0.5 μl aliquots were taken after 0, 5, 10, 20, 40 and 60 minutes and were spotted on 10×10 cm PEI cellulose sheets. The plates were then placed in a chamber containing 1 M NaCl (solvent) allowing the migration of deoxyadenosine-5'-triphosphate (dATP), deoxyadenosine-5'-diphosphate (dADP), deoxyadenosine-5'-monophosphate (dAMP) and inorganic phosphate (P$_i$). When the buffer front reached the top of the PEI cellulose sheets, they were removed from the chamber, dried and exposed for 6 minutes to X-ray film and developed.

Figure 4:
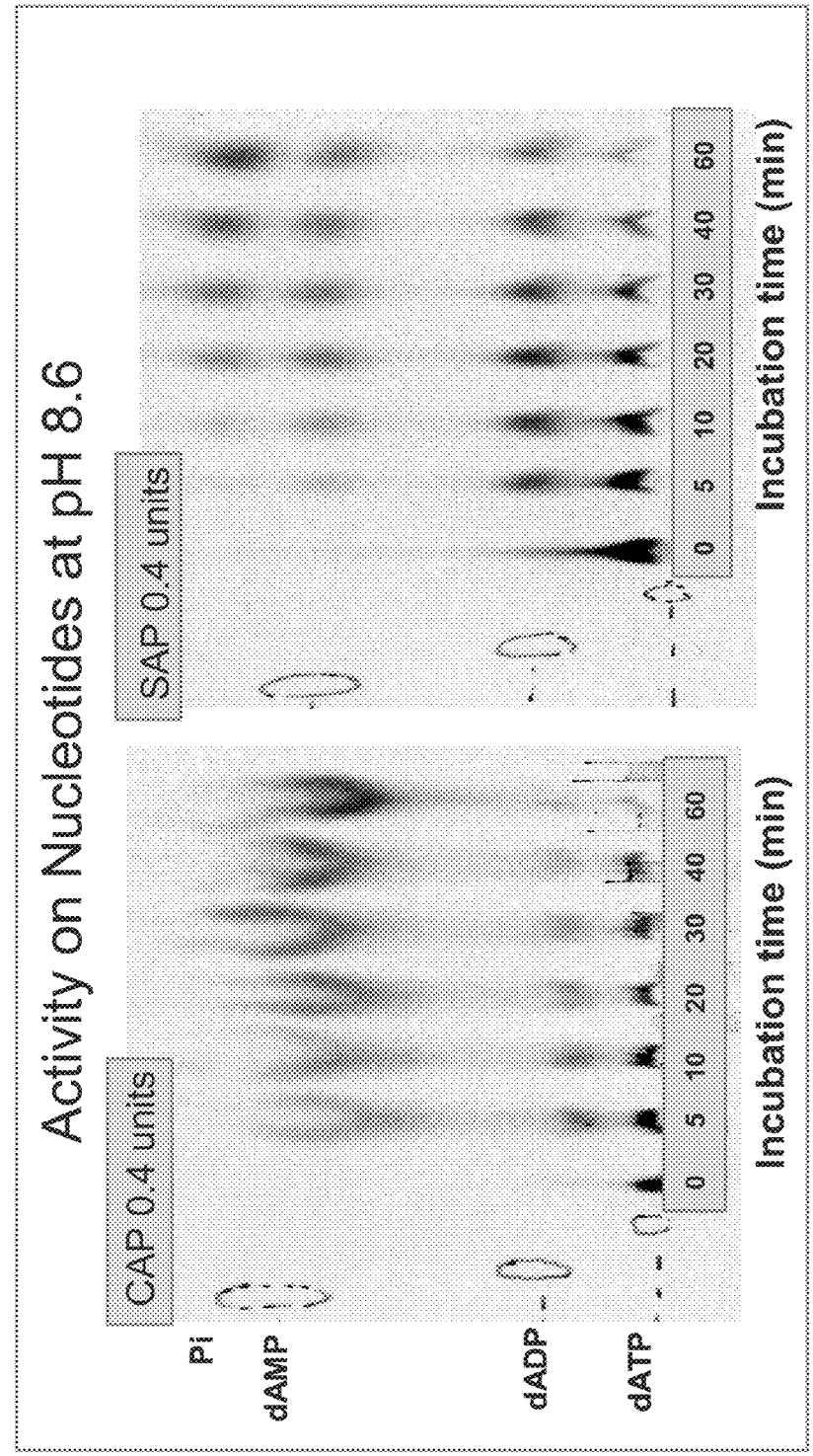
FIG. 4. Activity of *Colwellia psychrerythraea* Alkaline Phosphatase using dATP as substrate in "PCR" Buffer.

As shown in FIG. 4, incubation of labeled dATP with 0.4 units of CAP revealed a similar level of degradation after 5 minutes incubation at 37° C. compared to 0.4 units of SAP. CAP had a similar efficiency level of dATP degradation compared to SAP when "PCR" buffer was used as reaction buffer.

It is to be understood that the above description is intended to be illustrative and not restrictive. Many variations of the foregoing will be apparent to those of skill in the relevant fields of study. The scope of the disclosed methods and compositions should be determined with reference to the appended claims, along with the full scope of equivalents to which such claims are entitled. All cited references, including patent and non-patent literature, are incorporated herewith by reference in their entireties to the same extent as if each reference were individually and specifically indicated to be incorporated by reference and were set forth in its entirety herein, and for all purposes.

---

We claim:

1. An isolated nucleic acid comprising:
   a) the sequence of SEQ ID NO:3; or
   b) a sequence which is at least 95% identical to SEQ ID NO:3;
   wherein the sequence further comprises a nucleic acid sequence encoding a hydrophilic repeating polypeptide sequence, wherein the hydrophilic repeating polypeptide sequence is selected from the group consisting of: HQ, HQHQ, SEQ ID NOS:4 and 8-14, and wherein the isolated nucleic acid encodes a polypeptide with dephosphorylation activity.

2. The sequence according to claim 1, consisting essentially of the sequence of SEQ ID NO:3, wherein the sequence further comprises a nucleic acid sequence encoding a hydrophilic repeating polypeptide sequence, wherein the hydrophilic repeating polypeptide sequence is selected from the group consisting of: HQ, HQHQ, SEQ ID NOS:4 and 8-14.

3. The sequence according to claim 1, consisting of SEQ ID NO:3, wherein the sequence further comprises a nucleic acid sequence encoding a hydrophilic repeating polypeptide sequence, wherein the hydrophilic repeating polypeptide sequence is selected from the group consisting of: HQ, HQHQ, SEQ ID NOS:4 and 8-14.

4. An isolated vector comprising:
   a) the sequence of SEQ ID NO:3; or
   b) a sequence which is at least 95% identical to SEQ ID NO:3;
   wherein the sequence further comprises a nucleic acid sequence encoding a hydrophilic repeating polypeptide sequence, wherein the hydrophilic repeating polypeptide sequence is selected from the group consisting of: HQ, HQHQ, SEQ ID NOS:4 and 8-14, and wherein the sequence encodes a polypeptide with dephosphorylation activity.

5. An isolated bacterial cell comprising a vector, wherein said vector comprises:
   a) the sequence of SEQ ID NO:3; or
   b) a sequence which is at least 95% identical to SEQ ID NO:3;
   wherein the sequence further comprises a nucleic acid sequence encoding a hydrophilic repeating polypeptide sequence, wherein the hydrophilic repeating polypeptide sequence is selected from the group consisting of: HQ, HQHQ, SEQ ID NOS:4 and 8-14, and wherein the sequence encodes a polypeptide with dephosphorylation activity.

6. The isolated nucleic acid according to claim 1, wherein the nucleic acid sequence encoding the hydrophilic repeating polypeptide sequence is upstream of the sequence of SEQ ID NO:3 or the sequence which is at least 95% identical to SEQ ID NO:3.

7. The isolated nucleic acid according to claim 1, wherein the nucleic acid sequence encoding the hydrophilic repeating polypeptide sequence is downstream of the sequence of SEQ ID NO:3 or the sequence which is at least 95% identical to SEQ ID NO:3.

8. A nucleic acid comprising the sequence of SEQ ID NO:3, wherein the sequence further comprises a nucleic acid sequence encoding a hydrophilic repeating polypeptide sequence, and wherein the hydrophilic repeating polypeptide sequence is selected from the group consisting of: HQ, HQHQ, SEQ ID NOS: 4 and 8-14.

9. A vector comprising the sequence of SEQ ID NO:3, wherein the sequence further comprises a nucleic acid sequence encoding a hydrophilic repeating polypeptide sequence, and wherein the hydrophilic repeating polypeptide sequence is selected from the group consisting of: HQ, HQHQ, SEQ ID NOS:4 and 8-14.

10. A bacterial cell comprising a vector, wherein the vector comprises the sequence of SEQ ID NO:3, wherein the sequence further comprises a nucleic acid sequence encoding a hydrophilic repeating polypeptide sequence, and wherein the hydrophilic repeating polypeptide sequence is selected from the group consisting of: HQ, HQHQ, SEQ ID NOS:4 and 8-14.

11. A nucleic acid comprising:
   a) the sequence which is fully complementary to SED ID NO:3; or
   b) the sequence which hybridizes to SEQ ID NO:3 under stringent conditions, wherein the stringent conditions comprise a salt concentration of less than 1 M and a temperature of at least 25° C.;

wherein the sequence further comprises a first nucleic acid sequence, wherein the first nucleic acid sequence is fully complementary to a second nucleic acid sequence, wherein the second nucleic acid sequence encodes a hydrophilic repeating polypeptide sequence, and wherein the hydrophilic repeating polypeptide sequence is selected from the group consisting of: HQ, HQHQ, SEQ ID NOS:4 and 8-14.

12. A vector comprising:
a) the sequence which is fully complementary to SED ID NO:3; or
b) the sequence which hybridizes to SEQ ID NO:3 under stringent conditions, wherein the stringent conditions comprise a salt concentration of less than 1 M and a temperature of at least 25° C.;

wherein the sequence further comprises a first nucleic acid sequence, wherein the first nucleic acid sequence is fully complementary to a second nucleic acid sequence, wherein the second nucleic acid sequence encodes a hydrophilic repeating polypeptide sequence, and wherein the hydrophilic repeating polypeptide sequence is selected from the group consisting of: HQ, HQHQ, SEQ ID NOS:4 and 8-14.

13. A bacterial cell comprising a vector, wherein said vector comprises:
a) the sequence which is fully complementary to SED ID NO:3; or
b) the sequence which hybridizes to SEQ ID NO:3 under stringent conditions, wherein the stringent conditions comprise a salt concentration of less than 1 M and a temperature of at least 25° C.;

wherein the sequence further comprises a first nucleic acid sequence, wherein the first nucleic acid sequence is fully complementary to a second nucleic acid sequence, wherein the second nucleic acid sequence encodes a hydrophilic repeating polypeptide sequence, and wherein the hydrophilic repeating polypeptide sequence is selected from the group consisting of: HQ, HQHQ, SEQ ID NOS:4 and 8-14.

* * * * *

SEQUENCE LISTING

<160> NUMBER OF SEQ ID NOS: 16

<210> SEQ ID NO 1
<211> LENGTH: 2060
<212> TYPE: DNA
<213> ORGANISM: Colwellia psychrerythraea 34H

<400> SEQUENCE: 1

```
atgaaaaaac tactttccgc cgtttttgtc accctcacat tgggtgcttg tactaccact      60
gaacagtcta gtgatatttc atctgataac tcagtagccc caaattcaca aagcagccct     120
aaaaatatca tcatgatcgt aggcgatggt atgggaccag cttataccac tgcttatcgt     180
tatttcaatg atgacccgac aacagctgaa attgaacaaa gtgtatttga taaacattat     240
gtcggctcaa gtagtaccta cccagcaaaa atgtctgggt acatcactga ttcagctgct     300
gctgcaacag cgctagcgac aggtgtaaaa acttataatg atgcgatatc tgttgatact     360
aataaaaagt cgcttttgac tgttttagag tgggccaaac agcaaggtaa aaaaacaggt     420
gtcgttgtta cttctcagat aaatcatgca actcctgcct cttatctttc tcataatgaa     480
aacagaaata actataacgc tattgctgat agttatatcg acaatggcat aaaagccgat     540 gtttatttg gtggcggctg gaaatacttt attcgagaag accgtaattt agtcaacgaa     600
tttaaagcag ctggttttca atatatagat gattataaac aattatcaac actgaaatta     660
aataaaccgg tactcggtct ttttggcgat agcggtttac cttgggccct agacgataaa     720
gaaaaacatc gtttgtcgtt aatgacaaag gcagctacaa aacagcttaa aaatcccaat     780
ggttacttta tgttagttga agccagtcaa atcgattggg gtggacatgg acgagatatt     840
ggcgcggcta tggctgaaat ggacgacctt gcaaaaacaa tcgctttct agaagagtat     900 gtcgctaaaa atccagatac cttagttgta cttacagcag atcatagtac aggaggcctc     960
```

| | |
|---|---|
| agtattggaa gaaaaacagc tatgtctaac aaagacatac acagtaaata tttatggcaa | 1020 |
| cctgagatac tacgaacact gccccttttct cctgaaacgt ttgccaaaac ctttgctaac | 1080 |
| aacaacctga ctctgcaaca ggtcaatgag gtattaaagt ttgagatatc ttctgatgat | 1140 |
| atggcgttgt tattacagtc aaaaaaagag ggtataaaaa tataccaaca gttatcagca | 1200 |
| gaacaaaaac aaaaaaaatg ggcacctaaa gctgaaggac ctattttgat agcaattaaa | 1260 |
| aaaatcatag acataaagac aaacactggc tggggttcaa ttagtcattc gggtacacat | 1320 |
| accgcagtgg atgtacccgt ctatgccttt ggtaaaggaa gtgagcaatt taagggcaa | 1380 |
| atagataata ctgatattgc caaaaagata tttactttac taggtaaaaa gcatcaacat | 1440 |
| caacatcaat agcaaaagca attaactgtt gagcgaaaat tgcatcgtcg gacagaacgt | 1500 |
| aattagttcc aagatctggc tcagggtgac ctgacttgac ctaacctgga gccggcaagg | 1560 |
| gctcaagcct tccaccgctc tagcgctctc ttcccatcca ctccaaggac tgcagaggga | 1620 |
| atttcctttt ggcgcggagg gcagtcgctc cgagggacac cagaggatct cgtctgcagt | 1680 |
| gttgcttcca ccaccaggga cacgagctgg agtgagcaaa ccaacatgtc agagtgggag | 1740 |
| tcctactaca aaactgaggg cgaggaagag gaagaggatg aggagagccc cgacacaggt | 1800 |
| ggagaatata aatattcatg aagagatagc ttgatttttc tggttgatgc ctccagtgct | 1860 |
| atgttctaat ctcagggtga agatgaactc cacccttttg aaatgagcat ccagtgtatt | 1920 |
| cagagtgtgt acacctagta gatcataagc agcgatccgg atctactagc attggtgttc | 1980 |
| tatggaaccc gagaaagatc aaatatttat gaatctcaaa aatatattg tcttactagg | 2040 |
| attgggacaa cccatgcgct | 2060 |

<210> SEQ ID NO 2
<211> LENGTH: 434
<212> TYPE: DNA
<213> ORGANISM: Colwellia psychrerythraea 34H
<220> FEATURE:
<221> NAME/KEY: misc_feature
<222> LOCATION: (411)..(411)
<223> OTHER INFORMATION: n is a, c, g, or t

<400> SEQUENCE: 2

| | |
|---|---|
| ggttaactcg tctcctcccg cggttcaagt ccatcgatct caacaagccc attgacaagc | 60 |
| ggatctacaa ggggacccag cccacctgcc acgacttcaa ccagttcaca gctgccacag | 120 |
| agaccatttc cctgctggtg ggcttctctg ccggccaggt gcagtatctg gacctcatca | 180 |
| agaaagacac cagcaagcta ttcaatgaag agggcatctc ctcccaacca ggcagctccc | 240 |
| ccagtggcac tgtggtgtga atgtggatg tcccatgttc ccggcctcct agccataacc | 300 |
| ctccccgctg acctcaagaa tcactgtatt aacaagacta atcatgatgg aaggactgct | 360 |
| ccaagcccca cgctgcacac atactggggg tccataggtt ggccagcatg nggatgtagt | 420 |
| gcctgtgtgg cttg | 434 |

<210> SEQ ID NO 3
<211> LENGTH: 1434
<212> TYPE: DNA
<213> ORGANISM: Colwellia psychrerythraea 34H

<400> SEQUENCE: 3

| | |
|---|---|
| atgaaaaaac tactttccgc cgttttgtc acc

-continued

```
tatttcaatg atgacccgac aacagctgaa attgaacaaa gtgtatttga taaacattat    240
gtcggctcaa gtagtaccta cccagcaaaa atgtctgggt acatcactga ttcagctgct    300
gctgcaacag cgctagcgac aggtgtaaaa acttataatg atgcgatatc tgttgatact    360
aataaaaagt cgcttttgac tgttttagag tgggccaaac agcaaggtaa aaaaacaggt    420
gtcgttgtta cttctcagat aaatcatgca actcctgcct cttatctttc tcataatgaa    480
aacagaaata actataacgc tattgctgat agttatatcg acaatggcat aaaagccgat    540 gtttatttg gtggcggctg gaaatacttt attcgagaag accgtaattt agtcaacgaa    600
tttaaagcag ctggttttca atatatagat gattataaac aattatcaac actgaaatta    660
aataaaccgg tactcggtct ttttggcgat agcggtttac cttgggccct agacgataaa    720
gaaaaacatc gtttgtcgtt aatgacaaag gcagctacaa aacagcttaa aaatcccaat    780
ggttacttta tgttagttga agccagtcaa atcgattggg gtggacatgg acgagatatt    840
ggcgcggcta tggctgaaat ggacgacctt gcaaaaacaa tcgcttttct agaagagtat    900
gtcgctaaaa atccagatac cttagttgta cttacagcag atcatagtac aggaggcctc    960
agtattggaa gaaaaacagc tatgtctaac aaagacatac acagtaaata tttatggcaa   1020
cctgagatac tacgaacact gccccttct cctgaaacgt tgccaaaac ctttgctaac    1080 aacaacctga ctctgcaaca ggtcaatgag gtattaaagt ttgagatatc ttctgatgat   1140
atggcgttgt tattacagtc aaaaaaagag ggtataaaaa tataccaaca gttatcagca   1200
gaacaaaaac aaaaaaaatg ggcacctaaa gctgaaggcc ctatttgat agcaattaaa    1260 aaaatcatag acataaagac aaacactggc tggggttcaa ttagtcattc gggtacacat   1320
accgcagtgg atgtacccgt ctatgccttt ggtaaaggaa gtgagcaatt taaggggcaa   1380
atagataata ctgatattgc caaaaagata tttactttac taggtaaaaa gtag         1434
```

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

His Gln His Gln His Gln
1               5

<210> SEQ ID NO 5
<211> LENGTH: 483
<212> TYPE: PRT
<213> ORGANISM: Colwellia psychrerythraea 34H

<400> SEQUENCE: 5

Met Lys Lys Leu Leu Ser Ala Val Phe Val Thr Leu Thr Leu Gly Ala
1               5                   10                  15

Cys Thr Thr Thr Glu Gln Ser Ser Asp Ile Ser Ser Asp Asn Ser Val
                20                  25                  30

Ala Pro Asn Ser Gln Ser Ser Pro Lys Asn Ile Ile Met Ile Val Gly
            35                  40                  45

Asp Gly Met Gly Pro Ala Tyr Thr Thr Ala Tyr Arg Tyr Phe Asn Asp
        50                  55                  60

Asp Pro Thr Thr Ala Glu Ile Glu Gln Ser Val Phe Asp Lys His Tyr
    65                  70                  75                  80

Val Gly Ser Ser Ser Thr Tyr Pro Ala Lys Met Ser Gly Tyr Ile Thr 85                  90                  95
Asp Ser Ala Ala Ala Thr Ala Leu Ala Thr Gly Val Lys Thr Tyr
                100                 105                 110

Asn Asp Ala Ile Ser Val Asp Thr Asn Lys Lys Ser Leu Leu Thr Val
            115                 120                 125

Leu Glu Trp Ala Lys Gln Gln Gly Lys Lys Thr Gly Val Val Val Thr
        130                 135                 140

Ser Gln Ile Asn His Ala Thr Pro Ala Ser Tyr Leu Ser His Asn Glu
145                 150                 155                 160

Asn Arg Asn Asn Tyr Asn Ala Ile Ala Asp Ser Tyr Ile Asp Asn Gly
                165                 170                 175

Ile Lys Ala Asp Val Tyr Phe Gly Gly Gly Trp Lys Tyr Phe Ile Arg
            180                 185                 190

Glu Asp Arg Asn Leu Val Asn Glu Phe Lys Ala Ala Gly Phe Gln Tyr
        195                 200                 205

Ile Asp Asp Tyr Lys Gln Leu Ser Thr Leu Lys Leu Asn Lys Pro Val
210                 215                 220

Leu Gly Leu Phe Gly Asp Ser Gly Leu Pro Trp Ala Leu Asp Asp Lys
225                 230                 235                 240

Glu Lys His Arg Leu Ser Leu Met Thr Lys Ala Ala Thr Lys Gln Leu
                245                 250                 255

Lys Asn Pro Asn Gly Tyr Phe Met Leu Val Glu Ala Ser Gln Ile Asp
            260                 265                 270

Trp Gly Gly His Gly Arg Asp Ile Gly Ala Ala Met Ala Glu Met Asp
        275                 280                 285

Asp Leu Ala Lys Thr Ile Ala Phe Leu Glu Glu Tyr Val Ala Lys Asn
290                 295                 300

Pro Asp Thr Leu Val Val Leu Thr Ala Asp His Ser Thr Gly Gly Leu
305                 310                 315                 320

Ser Ile Gly Arg Lys Thr Ala Met Ser Asn Lys Asp Ile His Ser Lys
                325                 330                 335

Tyr Leu Trp Gln Pro Glu Ile Leu Arg Thr Leu Pro Leu Ser Pro Glu
            340                 345                 350

Thr Phe Ala Lys Thr Phe Ala Asn Asn Asn Leu Thr Leu Gln Gln Val
        355                 360                 365

Asn Glu Val Leu Lys Phe Glu Ile Ser Ser Asp Met Ala Leu Leu
370                 375                 380

Leu Gln Ser Lys Lys Glu Gly Ile Lys Ile Tyr Gln Gln Leu Ser Ala
385                 390                 395                 400

Glu Gln Lys Gln Lys Lys Trp Ala Pro Lys Ala Glu Gly Pro Ile Leu
                405                 410                 415

Ile Ala Ile Lys Lys Ile Ile Asp Ile Lys Thr Asn Thr Gly Trp Gly
            420                 425                 430

Ser Ile Ser His Ser Gly Thr His Thr Ala Val Asp Val Pro Val Tyr
        435                 440                 445

Ala Phe Gly Lys Gly Ser Glu Gln Phe Lys Gly Gln Ile Asp Asn Thr
450                 455                 460

Asp Ile Ala Lys Lys Ile Phe Thr Leu Leu Gly Lys Lys His Gln His
465                 470                 475                 480

Gln His Gln

<210> SEQ ID NO 6
<211> LENGTH: 28
<212> TYPE: DNA

```
<213> ORGANISM: Colwellia psychrerythraea 34H

<400> SEQUENCE: 6
atccatatga aaaaactgct gtccgccg                                          28

<210> SEQ ID NO 7
<211> LENGTH: 47
<212> TYPE: DNA
<213> ORGANISM: Colwellia psychrerythraea 34H

<400> SEQUENCE: 7
cgcccgggct actgatgttg atgttgatgc ttttacctgt agtaaagt                    47

<210> SEQ ID NO 8
<211> LENGTH: 20
<212> TYPE: PRT
<213> ORGANISM: Artificial sequence
<220> FEATURE:
<223> OTHER INFORMATION: Synthetic

<400> SEQUENCE: 8

His Gln His Gln His Gln His Gln His Gln His Gln His Gln His Gln
1               5                   10                  15

His Gln His Gln
        20

<210> SEQ ID NO 9
<211> LENGTH: 8
<212> TYPE: PRT
<213> ORGANISM: Artificial sequence
<220> FEATURE:
<223> OTHER INFORMATION: Synthetic

<400> SEQUENCE: 9

His Gln His Gln His Gln His Gln
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic

<400> SEQUENCE: 10

His Gln His Gln His Gln His Gln His Gln
1               5                   10

<210> SEQ ID NO 11
<211> LENGTH: 12
<212> TYPE: PRT
<213> ORGANISM: Artificial sequence
<220> FEATURE:
<223> OTHER INFORMATION: Synthetic

<400> SEQUENCE: 11

His Gln His Gln His Gln His Gln His Gln His Gln
1               5                   10

<210> SEQ ID NO 12
<211> LENGTH: 14
<212> TYPE: PRT
<213> ORGANISM: Artificial sequence
<220> FEATURE:
<223> OTHER INFORMATION: Synthetic

<400> SEQUENCE: 12
```

```
His Gln His Gln His Gln His Gln His Gln His Gln His Gln
1               5                   10
```

<210> SEQ ID NO 13
<211> LENGTH: 16
<212> TYPE: PRT
<213> ORGANISM: Artificial sequence
<220> FEATURE:
<223> OTHER INFORMATION: Synthetic

<400> SEQUENCE: 13

```
His Gln His Gln His Gln His Gln His Gln His Gln His Gln His Gln
1               5                   10                  15
```

<210> SEQ ID NO 14
<211> LENGTH: 18
<212> TYPE: PRT
<213> ORGANISM: Artificial sequence
<220> FEATURE:
<223> OTHER INFORMATION: Synthetic

<400> SEQUENCE: 14

```
His Gln His Gln His Gln His Gln His Gln His Gln His Gln His Gln
1               5                   10                  15

His Gln
```

<210> SEQ ID NO 15
<211> LENGTH: 477
<212> TYPE: PRT
<213> ORGANISM: Colwellia psychrerythraea 34H

<400> SEQUENCE: 15

```
Met Lys Lys Leu Leu Ser Ala Val Phe Val Thr Leu Thr Leu Gly Ala
1               5                   10                  15

Cys Thr Thr Thr Glu Gln Ser Ser Asp Ile Ser Ser Asp Asn Ser Val
                20                  25                  30

Ala Pro Asn Ser Gln Ser Ser Pro Lys Asn Ile Ile Met Ile Val Gly
            35                  40                  45

Asp Gly Met Gly Pro Ala Tyr Thr Thr Ala Tyr Arg Tyr Phe Asn Asp
        50                  55                  60

Asp Pro Thr Thr Ala Glu Ile Glu Gln Ser Val Phe Asp Lys His Tyr
65                  70                  75                  80

Val Gly Ser Ser Ser Thr Tyr Pro Ala Lys Met Ser Gly Tyr Ile Thr
                85                  90                  95

Asp Ser Ala Ala Ala Ala Thr Ala Leu Ala Thr Gly Val Lys Thr Tyr
            100                 105                 110

Asn Asp Ala Ile Ser Val Asp Thr Asn Lys Lys Ser Leu Leu Thr Val
        115                 120                 125

Leu Glu Trp Ala Lys Gln Gln Gly Lys Lys Thr Gly Val Val Val Thr
130                 135                 140

Ser Gln Ile Asn His Ala Thr Pro Ala Ser Tyr Leu Ser His Asn Glu
145                 150                 155                 160

Asn Arg Asn Asn Tyr Asn Ala Ile Ala Asp Ser Tyr Ile Asp Asn Gly
                165                 170                 175

Ile Lys Ala Asp Val Tyr Phe Gly Gly Gly Trp Lys Tyr Phe Ile Arg
            180                 185                 190

Glu Asp Arg Asn Leu Val Asn Glu Phe Lys Ala Ala Gly Phe Gln Tyr
        195                 200                 205

Ile Asp Asp Tyr Lys Gln Leu Ser Thr Leu Lys Leu Asn Lys Pro Val
```

```
                  210                 215                 220
Leu Gly Leu Phe Gly Asp Ser Gly Leu Pro Trp Ala Leu Asp Asp Lys
225                 230                 235                 240

Glu Lys His Arg Leu Ser Leu Met Thr Lys Ala Ala Thr Lys Gln Leu
                245                 250                 255

Lys Asn Pro Asn Gly Tyr Phe Met Leu Val Glu Ala Ser Gln Ile Asp
            260                 265                 270

Trp Gly Gly His Gly Arg Asp Ile Gly Ala Ala Met Ala Glu Met Asp
        275                 280                 285

Asp Leu Ala Lys Thr Ile Ala Phe Leu Glu Glu Tyr Val Ala Lys Asn
290                 295                 300

Pro Asp Thr Leu Val Val Leu Thr Ala Asp His Ser Thr Gly Gly Leu
305                 310                 315                 320

Ser Ile Gly Arg Lys Thr Ala Met Ser Asn Lys Asp Ile His Ser Lys
                325                 330                 335

Tyr Leu Trp Gln Pro Glu Ile Leu Arg Thr Leu Pro Leu Ser Pro Glu
            340                 345                 350

Thr Phe Ala Lys Thr Phe Ala Asn Asn Asn Leu Thr Leu Gln Gln Val
        355                 360                 365

Asn Glu Val Leu Lys Phe Glu Ile Ser Ser Asp Asp Met Ala Leu Leu
370                 375                 380

Leu Gln Ser Lys Lys Glu Gly Ile Lys Ile Tyr Gln Gln Leu Ser Ala
385                 390                 395                 400

Glu Gln Lys Gln Lys Lys Trp Ala Pro Lys Ala Glu Gly Pro Ile Leu
                405                 410                 415

Ile Ala Ile Lys Lys Ile Ile Asp Ile Lys Thr Asn Thr Gly Trp Gly
            420                 425                 430

Ser Ile Ser His Ser Gly Thr His Thr Ala Val Asp Val Pro Val Tyr
        435                 440                 445

Ala Phe Gly Lys Gly Ser Glu Gln Phe Lys Gly Gln Ile Asp Asn Thr
    450                 455                 460

Asp Ile Ala Lys Lys Ile Phe Thr Leu Leu Gly Lys Lys
465                 470                 475

<210> SEQ ID NO 16
<211> LENGTH: 1452
<212> TYPE: DNA
<213> ORGANISM: Colwellia psychrerythraea 34H

<400> SEQUENCE: 16
atgaaaaaac tactttccgc cgttttgtc accctcacat tgggtgcttg tactaccact      60
gaacagtcta gtgatatttc atctgataac tcagtagccc caaattcaca agcagccct    120 aaaaatatca tcatgatcgt aggcgatggt atgggaccag cttataccac tgcttatcgt    180
tatttcaatg atgaccccgac aacagctgaa attgaacaaa gtgtatttga taaacattat    240
gtcggctcaa gtagtaccta cccagcaaaa atgtctgggt acatcactga ttcagctgct    300
gctgcaacag cgctagcgac aggtgtaaaa acttataatg atgcgatatc tgttgatact    360
aataaaaagt cgcttttgac tgttttagag tgggccaaac agcaaggtaa aaaacaggt    420 gtcgttgtta cttctcagat aaatcatgca actcctgcct cttatctttc tcataatgaa    480
aacagaaata actataacgc tattgctgat agttatatcg acaatggcat aaaagccgat    540
gtttattttg gtggcggctg gaaatacttt attcgagaag accgtaattt agtcaacgaa    600
tttaaagcag ctggttttca atatatagat gattataaac aattatcaac actgaaatta    660
```

-continued

```
aataaaccgg tactcggtct ttttggcgat agcggtttac cttgggccct agacgataaa      720
gaaaaacatc gtttgtcgtt aatgacaaag gcagctacaa aacagcttaa aaatcccaat      780
ggttacttta tgttagttga agccagtcaa atcgattggg gtggacatgg acgagatatt      840
ggcgcggcta tggctgaaat ggacgacctt gcaaaaacaa tcgcttttct agaagagtat      900
gtcgctaaaa atccagatac cttagttgta cttacagcag atcatagtac aggaggcctc      960
agtattggaa gaaaaacagc tatgtctaac aaagacatac acagtaaata tttatggcaa     1020
cctgagatac tacgaacact gccccttttct cctgaaacgt ttgccaaaac ctttgctaac    1080
aacaacctga ctctgcaaca ggtcaatgag gtattaaagt ttgagatatc ttctgatgat     1140
atggcgttgt tattacagtc aaaaaaagag ggtataaaaa tataccaaca gttatcagca     1200
gaacaaaaac aaaaaaaatg ggcacctaaa gctgaaggac ctattttgat agcaattaaa     1260
aaaatcatag acataaagac aaacactggc tggggttcaa ttagtcattc gggtacacat     1320
accgcagtgg atgtacccgt ctatgccttt ggtaaaggaa gtgagcaatt taaggggcaa     1380
atagataata ctgatattgc caaaaagata tttactttac taggtaaaaa gcatcaacat     1440
caacatcaat ag                                                         1452
```